United States Patent
Klepp (10) Patent No.: US 9,848,784 B2
(45) Date of Patent: Dec. 26, 2017

(54) METHOD FOR DETERMINING THE PHYSICAL AND/OR PSYCHOLOGICAL STATE OF A SUBJECT

(71) Applicant: Tracer Systems GmbH, Stainz (AT)

(72) Inventor: Nikolaus Klepp, Gmunden (AT)

(73) Assignee: Tracer Systems GmbH, Stainz (AT)

( * ) Notice: Subject to any disclaimer, the term of this patent is extended or adjusted under 35 U.S.C. 154(b) by 24 days.

(21) Appl. No.: 14/377,248

(22) PCT Filed: Feb. 8, 2013

(86) PCT No.: PCT/EP2013/052573
§ 371 (c)(1),
(2) Date: Aug. 7, 2014

(87) PCT Pub. No.: WO2013/117710
PCT Pub. Date: Aug. 15, 2013

(65) Prior Publication Data
US 2015/0282722 A1    Oct. 8, 2015

(30) Foreign Application Priority Data

Feb. 8, 2012   (EP) ..................... 12154578
Feb. 9, 2012   (EP) ..................... 12154764

(51) Int. Cl.
*A61B 5/024*   (2006.01)
*A61B 5/00*    (2006.01)
(Continued)

(52) U.S. Cl.
CPC ........ *A61B 5/02405* (2013.01); *A61B 5/0456* (2013.01); *A61B 5/165* (2013.01);
(Continued)

(58) Field of Classification Search
CPC ... A61B 5/02405; A61B 5/0456; A61B 5/165; A61B 5/4035; A61B 5/4884; A61B 5/7246; A61B 5/7264; A61B 5/7282
(Continued)

(56) References Cited

U.S. PATENT DOCUMENTS 5,419,338 A * 5/1995 Sarma ................. A61B 5/0452
600/516
2009/0005696 A1   1/2009 Riftine
(Continued)

FOREIGN PATENT DOCUMENTS

DE   10 2006 053728 A1   3/2008

OTHER PUBLICATIONS

International Search Report of PCT/EP2013/052573, dated May 23, 2013.

*Primary Examiner* — Carl H Layno
*Assistant Examiner* — Erin M Piateski
(74) *Attorney, Agent, or Firm* — Collard & Roe, P.C.

(57) ABSTRACT

The invention relates to a method for determining the physical and/or psychological state of a subject. The heart rate variability (HRV) of the subject is analyzed in the time domain, wherein at least one frequency distribution of interbeat intervals (IBI) which are detected in at least one examination time period (1) is examined in the analysis. In order to obtain particularly significant and quickly interpretable information for this purpose, the frequency distribution is examined for a multimodal distribution.

17 Claims, 7 Drawing Sheets

(51) Int. Cl.
*A61B 5/16* (2006.01)
*A61B 5/0456* (2006.01)

(52) U.S. Cl.
CPC .......... *A61B 5/4035* (2013.01); *A61B 5/4884* (2013.01); *A61B 5/7246* (2013.01); *A61B 5/7264* (2013.01); *A61B 5/7282* (2013.01)

(58) Field of Classification Search
USPC ........................................................ 600/508
See application file for complete search history.

(56) References Cited

U.S. PATENT DOCUMENTS

2009/0192394 A1* 7/2009 Guttag ............... A61B 5/02405
600/509
2010/0174205 A1* 7/2010 Wegerif ............. A61B 5/02405
600/515

* cited by examiner

METHOD FOR DETERMINING THE PHYSICAL AND/OR PSYCHOLOGICAL STATE OF A SUBJECT

CROSS REFERENCE TO RELATED APPLICATIONS

This application is the National Stage of PCT/EP2013/052573 filed on Feb. 8, 2013, which claims priority under 35 U.S.C. §119 of European Application Nos. 12154578.4 filed on Feb. 8, 2012, and 12154764.0 filed on Feb. 9, 2012, the disclosures of which are incorporated by reference. The international application under PCT article 21(2) was not published in English.

TECHNICAL FIELD

The invention relates to a method for determination of the physical and/or psychological state of a subject, in that the heart rate variability (HRV) of the subject is subjected to analysis in the time domain, during which analysis at least one frequency distribution of interbeat intervals (IBI) recorded during at least one examination time period is investigated.

STATE OF THE ART

In order to determine the physical and/or psychological state of a subject, it is known from the state of the art to determine the resting pulse or the pulse frequency—possibly at different respiratory defaults—and, in particular, to put the results obtained in this connection in relation to comparison values. Such methods can possibly yield guideline values with regard to the state or the performance capacity of a subject, but they prove to be comparatively complicated, because the conditions under which the determination is carried out can only be standardized with difficulty. Furthermore, the results of such methods are only meaningful with limitations, last but not least because an average heart rate is determined, but this only represents a result of the heart beats on which it is based.

Furthermore, it is known (US2009/0005696A1, DE102006053728A1, US2010/0174205A1) to determine interbeat intervals (IBI), or, particularly, RR intervals of heart activity over a specific time period, and to calculate heart rate variability by way of quantification of the variations measured in this connection, in order to thereby be able to draw conclusions concerning the influence of the vegetative nervous system on heart activity and consequently conclusions concerning the psychological and physical state. It is specifically known that two persons who demonstrate the same heart rhythm can differ significantly in terms of their regulation state caused by the vegetative nervous system and thereby in their state of health and their performance capacity.

This measurement method of HRV analysis primarily differentiates between two different domains, analysis in the time domain and analysis in the frequency domain.

In an analysis in the frequency domain, the frequency components of which the variability in heart rate is composed are considered (see US2009/0005696A1). The measurement spectrum in question is divided up into multiple frequency bands, VLF (very low frequency), LF (low frequency), HF (high frequency), etc., on the basis of which an attempt is made to assess the psychological and physical state of the subject. However, analyses in the frequency domain are extremely disputed, because it is denied that they have the ability to reflect changes in the sympathetic and parasympathetic activity under physical stress, and thereby such methods can be carried out only in comparatively uncertain manner and are difficult to interpret with regard to their results.

In the case of known methods that carry out an analysis in the time domain, the distances between two consecutive IB intervals or RR intervals, or the difference between such adjacent intervals are considered (DE102006053728A1, US2010/0174205A1). For example, an attempt is made to represent the frequency of results of an IBI measurement in the form of a Gauss curve. Conclusions concerning the physical and/or psychological state of a subject are drawn from the location of this maximum or from the Gauss curve, the distribution of the classes surrounding this maximum, or the standard deviation and/or symmetry of the Gauss curve, etc. A further possibility for analysis in the time domain is the representation of the values determined in a scatter plot (e.g. Poincaré Plot or Lorenz Plot). The dimension of the HRV is derived from a geometric distribution shape that forms from time measurement data of the IBI intervals or RR intervals. However, such a method proves to be complicated—it is generally necessary to select the duration of the measurement to be comparatively long for the desired classification of a maximum, for example 30 minutes. Furthermore, such a method is also only meaningful with limitations. Among other things, while it is taken into consideration that the heart activity is characterized by differently variable RR interval lengths depending on the state of the subject, one proceeds essentially from one basic frequency, determined by a single mode, for its evaluation.

PRESENTATION OF THE INVENTION

The invention has therefore set itself the task of developing a method with which conclusions concerning the physical and/or psychological state of a subject can be drawn easily, quickly, and reproducibly. Furthermore, it should be possible to use the method according to the invention independently of parameters such as ambient temperature, time of day, etc., to a great extent.

The invention accomplishes the task in that the frequency distribution is investigated with regard to a multimodal distribution.

If the frequency distribution is investigated with regard to a multimodal distribution, particularly meaningful information concerning heart activity can be obtained, on the basis of which a conclusion concerning the psychological and/or physical state of a subject is possible.

In the method according to the invention, it can specifically be taken into consideration that the occurrence of multiple modal values or certain modal distributions can be an indication of a particularly disadvantageous regulation state of the heart by the vegetative nervous system—specifically even when two modal values having a very small difference with regard to the lengths of their interbeat intervals (IBI) can be identified, for example. In this connection, the manifestation, location, etc. of one or more additional modal values also does not necessarily play a role; simply the fact that more than one modal value or modal distributions can be identified can provide important information and can actually be used as a fundamental indicator for heart activity that deviates from a desirable regulation state of the heart. This can specifically be interpreted as a type of deviation from a basic frequency. It can therefore mean that the heart activity is determined not just by means of variability of the IBI lengths about what is called a basic oscillation, which basic oscillation is characterized by a certain bandwidth of IBI lengths about a maximum formed by particularly many measured interbeat interval lengths. Instead, the heart activity therefore forms multiple maxima of frequencies of interbeat intervals, which are particularly influenced by the vegetative nervous system, with regard to their lengths.

If RR intervals of the heart and/or distances between pulse waves are used as interbeat intervals, particularly precise and simple determination of the heart rate variability can occur. For the sake of completeness, it should be mentioned that RR interval refers to the distance between two R peaks of an electrocardiogram; of course, however, points and/or leads of an EKG can also be suitable for the method according to the invention. If the distances between pulse waves are used, particularly simple yet nevertheless precise determination can be made possible. Thus, for example, a determination of interbeat intervals can be carried out using known corresponding devices—ear clip sensors or finger sensors, which measure the light permeability of the skin with infrared, for example, or also hand pulse sensors can be mentioned as examples. Here, a possibility is to determine the calculated maximum of the pulse wave or also the beginning of a specific increase, for example.

If a classified frequency distribution is used, simplified representation, analysis and/or processing of the measurement values obtained can take place. Of course, it must be noted that the class boundaries or the class widths are established in such a manner that possible modal values do not intersect, superimpose, etc. and have any other negative influence on the method according to the invention. Of course, in this connection, it can also play a role what length of the examination time period is selected for measurement of interbeat intervals. A long-term measurement of 20 minutes and more, as this usually occurs in the state of the art, can clearly favor superimposition of possible modes or at least make the analysis significantly more difficult. It is advantageous if the method according to the invention therefore takes into consideration not only the number of identified maxima but also variability of the IBI about these maxima. The most varied methods are known for identifying such modes, among them threshold value analyses.

If the investigation of the frequency distribution takes place using a univariate statistical analysis, a meaningful analysis of the heart rate variability is possible in quick and simple manner. A histogram, in which the lengths of the IBI recorded during an examination period are entered in accordance with their frequency, should be mentioned as an example of this.

If the investigation of the frequency distribution takes place using a bivariate statistical analysis, then among other things, a more precise analysis of the HRV can result, because relationships of interbeat intervals can particularly be presented. If more than one manifestation is used for analysis, an improved conclusion concerning the heart activity can therefore take place.

If at least one interbeat interval with its subsequent interbeat interval is used for the bivariate statistical analysis, a particularly precise analysis of the HRV can be made possible, because among other things, it can be evident how suddenly the lengths of consecutive interbeat intervals change. Great variations in the lengths of interbeat intervals that occur one after the other can therefore lead to the assumption that the regulation state of the heart is in a comparatively imbalanced state, and this in turn can permit corresponding conclusions concerning the psychological and/or physical state of a subject. If interbeat intervals whose subsequent IBI, in each instance, differs significantly in terms of its length actually form a mode or multiple modes, a comparatively disadvantageous regulation state of the heart activity can therefore be assumed.

If the bivariate statistical analysis comprises classification of the frequency distribution as a function of the differences of two consecutive interbeat interval lengths, meaningful and, above all, easily interpreted information concerning the HRV or the vegetative nervous system of a subject can be obtained. In turn, on the basis of such an analysis, improved conclusions concerning the psychological and/or physical state of a subject can be provided, on the basis of which the state of health, the regeneration capacity, the ideal intensity of a physical training unit, and so forth, for example, can be better evaluated.

If a correction value as a function of the difference of their length is taken into consideration for the analysis of consecutive interbeat intervals, consecutive interbeat intervals whose length differs to a high degree, for example, can be taken into consideration in improved manner. In order to meet this requirement, which is given as an example, those consecutive interbeat intervals whose lengths are essentially the same are blanked out using a correction value—thereby making it possible to take a change in the basic frequency, for example, as it can occur during the course of an extended examination, due to external stimuli, into consideration in improved manner.

If the analysis of the heart rate variability takes into consideration the distance between modal values, the meaningfulness of the method according to the invention can be further improved. A great difference between two modal values that might be determined, with regard to the length of the IBI intervals, can permit the conclusion of comparatively disadvantageous heart rate variability, in accordance with the above explanations—specifically all the more disadvantageous, the greater this determined difference appears to be.

For further improvement of the evaluation of the heart rate variability, the analysis of the heart rate variability can take into consideration a ratio of the densities of the modal distributions, particularly the integrals of these densities. Therefore, for example, ratios of the modes relative to one another or also the amount proportions of the RR intervals related to the modes, in each instance, can be represented or evaluated more easily. This can also be suitable for scatter plots with consecutive interbeat intervals, whereby the duration of each interbeat interval of a specific measurement time period is entered as a function of the duration of the interbeat interval that follows it. In this connection, a graphic representation could yield a two-dimensional image in which the density of the modal distribution is indicated with colors or with height lines—of course, however, other representations of the method according to the invention would be possible, for example a three-dimensional representation. In this manner, a significantly faster or simplified analysis of the HRV would be made possible, specifically also taking into consideration the manifestation of multiple frequencies, or of their relationships, relations and/or dependence relative to one another.

In general, it can therefore be stated that the meaningfulness of the method according to the invention can be further improved if one parameter, in each instance, particularly the same parameter, is determined from at least two modal distributions, the comparison result of which parameter is taken into consideration in the analysis of the heart rate variability (HRV). As has already been mentioned above, these parameters can be modal values of the modal distributions, densities of the modal distributions, or also integrals of these densities, which are compared with regard to spacing, size, etc. Accordingly, it is the goal of the method according to the invention, among other things, to identify the possible occurrence of more than one mode in targeted manner, in order to draw conclusions concerning the regulation state of the heart on the basis of the information obtained in this manner. Therefore, even if only one basic oscillation appears to be present, this can be investigated further, in targeted manner—for example using a bivariate analysis, by means of adaptation of the classification of the frequency distribution, etc., in order to recognize any modes that might be present, and to compare specific parameters with regard to these modes with one another.

The analysis according to the invention can be further improved if the analysis data of the heart rate variability (HRV) are put into relation with comparison data of other subjects during the determination of the physical and/or psychological state of a subject. It should be mentioned that in this connection, it can be particularly advantageous to obtain information about the life circumstances of the subject when referring to corresponding comparison data. In this manner, not only can assessments of analyzed HRV be facilitated, but also any measures that might be required to improve HRV can be established and/or reviewed in simplified manner. Furthermore, it is of course possible to use analyses of different subjects or subject groups according to different criteria, in order to develop models in order to in turn draw conclusions concerning the physical and/or psychological state of a subject.

If the modal values of the frequency distribution are determined using a threshold value, it can be made possible, for example, to facilitate classification of a multimodal distribution and/or to represent it particularly clearly. This can also have the advantage that the measurement results that appear to be statistical outliers, last but not least on the basis of a measurement period of 20 minutes that is usual in the state of the art, can also be taken into consideration more easily.

The method according to the invention can be particularly informational if the frequency distributions of iriterbeat intervals recorded during at least two examination time periods are investigated, whereby different physical and/or psychological stress states are acting on the subject during the examination time periods. In this manner, for example, the adaptability of a subject to different stresses can be determined. It can also be determined in simplified manner what stress intensity—for example for physical training—best meets the requirements or the state of the subject. The effect of possible relaxation training, of a change in life habits can thereby be quickly and easily determined and/or optimized. For this purpose, it is only necessary to check changes in the heart rate variability and, in particular, in maxima that might be formed, at regular time intervals. In many cases, it can be assumed, for example, that a reduction in the distance between modal values that are determined should be evaluated positively, as a positive development. According to the invention, a comparatively short measurement period of the heart activity, in the range of several minutes, can be sufficient for a meaningful analysis.

It is advantageous that a correction value for a time domain analysis of the heart rate variability, for example for the parameters RMSSD and/or pNN50, can be calculated and taken into consideration using the investigation of the frequency distribution.

It should be mentioned that of course, the term subject is understood to mean a person, independent of age, gender, state of health or other characteristics.

BRIEF DESCRIPTION OF THE DRAWINGS

In the drawings, the object of the invention is explained in greater detail, as an example, using figures. These show.

WAYS TO IMPLEMENT THE INVENTION

For the sake of completeness, it should be mentioned that in the figures, RR intervals are investigated and represented, but that of course, it lies within the scope of the invention to also use other parameters and/or measurement methods for a determination of interbeat intervals.

Figure 1:
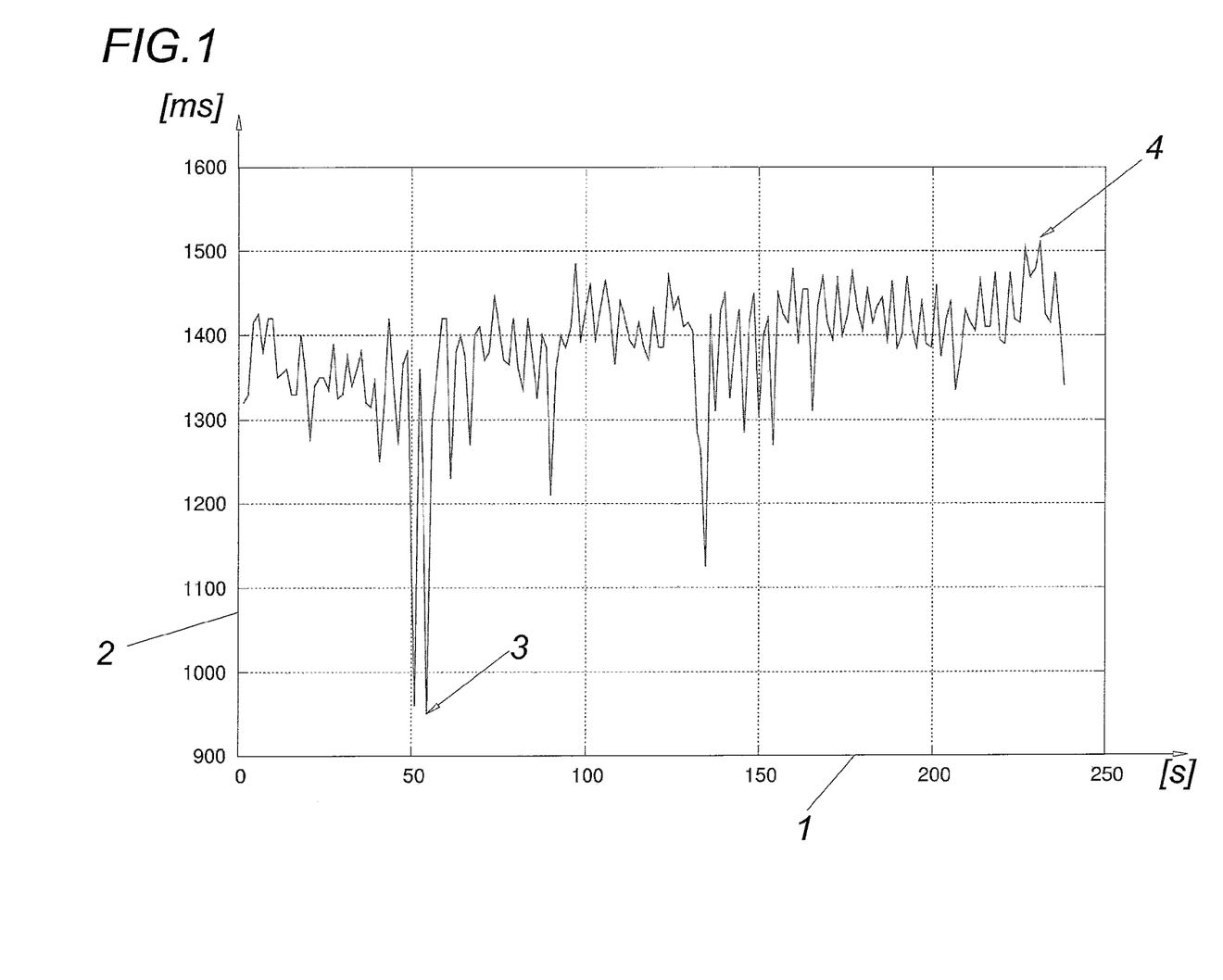
FIG. 1 a representation of RR interval lengths determined in a specific examination time period,
FIG. 2 a histogram of the RR intervals according to the results in FIG. 1,
FIG. 3 the RR intervals of the results in FIG. 1 as a scatter plot,
FIGS. 4 to 6 an example of a different RR interval determination corresponding to the representations according to FIGS. 1 to 3,
FIG. 7 a further graphic representation of a different measurement result, along with a histogram of RR interval pairs, plotted as a function of the difference of their lengths relative to one another.

According to FIG. 1, the RR intervals of consecutive heart beats of a subject recorded during an examination time period 1 are shown graphically. In this connection, the time lengths 2 of the RR intervals that occur along the x axis of the examination time period 1 in seconds [s] are plotted in milliseconds [ms], and consecutive RR intervals are connected with one another by means of a straight line. For example, the representation according to FIG. 1 can thereby show the minimal and maximal RR interval 3 and 4 of a specific time period. A different representation, for example as an RR tachogram, is also possible, but is not shown.

Figure 2:
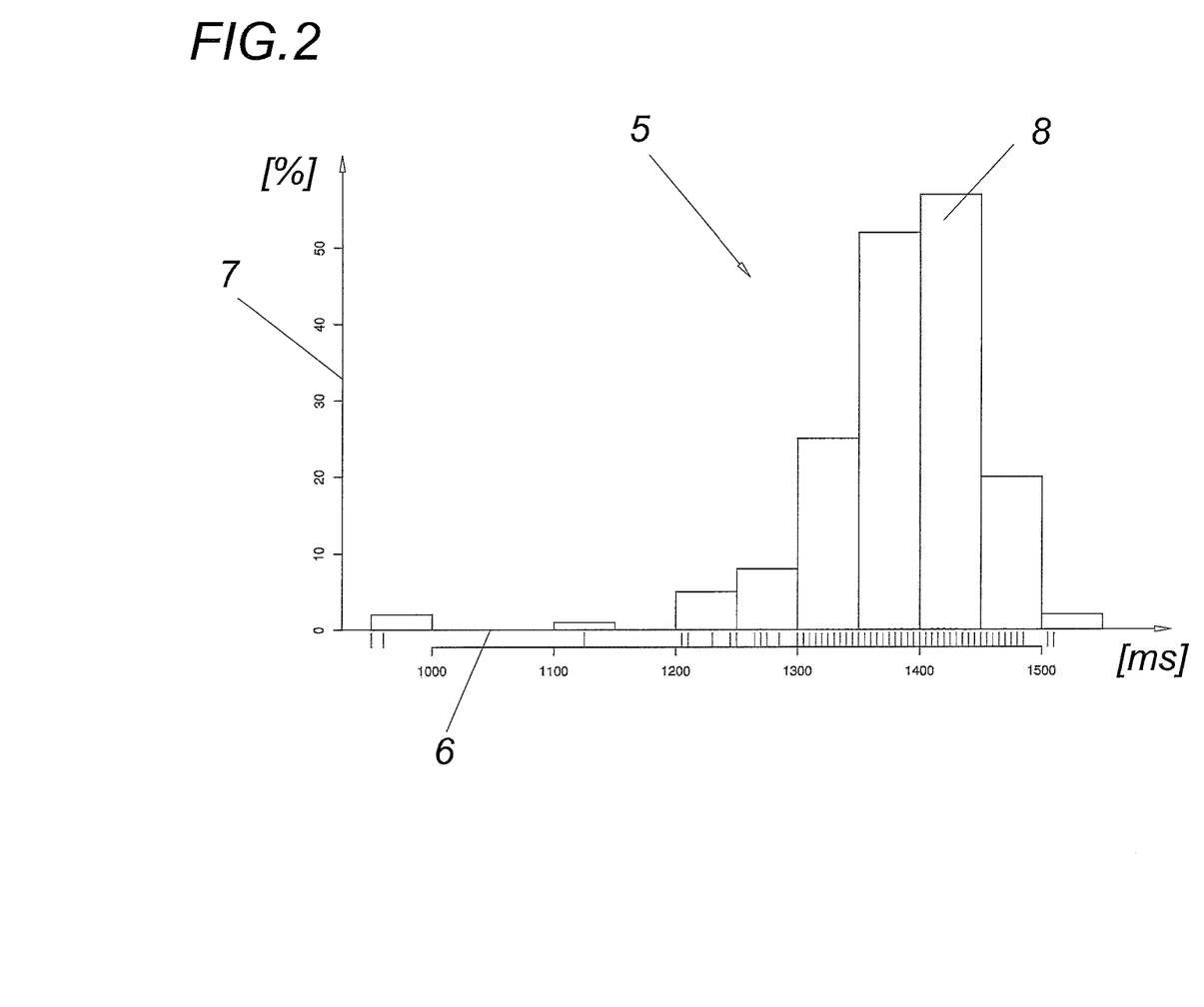

Likewise, a frequency distribution according to FIG. 2 can be derived from the values shown in FIG. 1. FIG. 2 represents a univariate statistical analysis in the time domain, in the form of a histogram 5, in which, for example, all the RR intervals that were determined during a specific time period are combined in 50 ms classes, whereby the x axis 6 characterizes the length of RR intervals in ms. The heights of these classes, shown as bars, result in accordance with the scaling of the y axis 7 and the number of RR intervals belonging to the class, in each instance, in this histogram. In this example, a modal value 8 can be recognized. The variation width of the lengths of the RR intervals can be derived from the number and height of the classes—for example also by means of evaluation as compared with comparison values. Such a histogram can be worked on further, for example in order to take the ratio of the densities of the modal distributions, particularly the integrals of these densities, into consideration; this is not shown in any detail in FIG. 2. If the frequency distribution shows merely one mode and an essentially normal, symmetrical density distribution—similar to a Gauss curve—one speaks of a comparatively good variability of the heart rates and a good state of a subject, in accordance with the state of the art.

Figure 3:
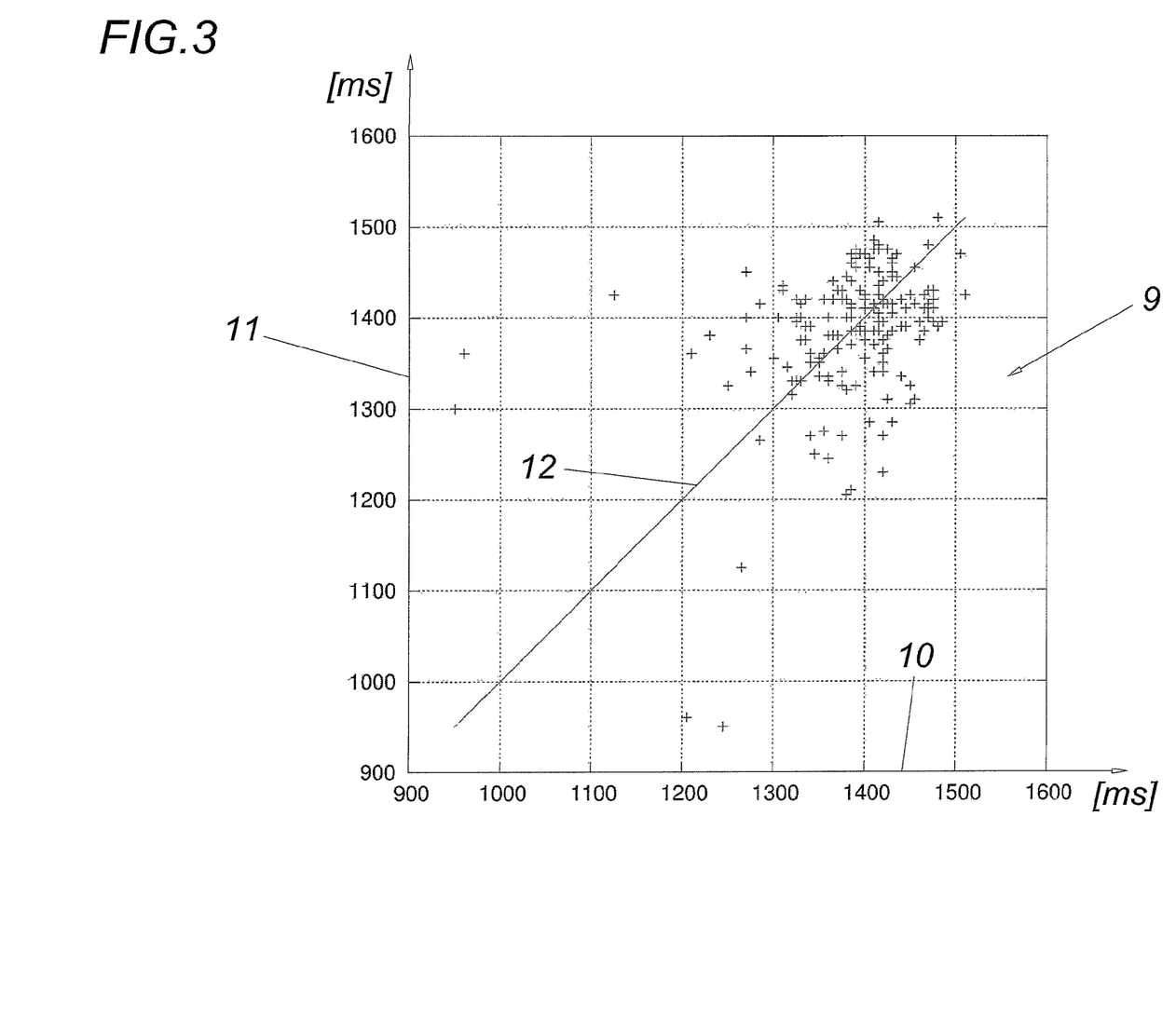
Figure 4:
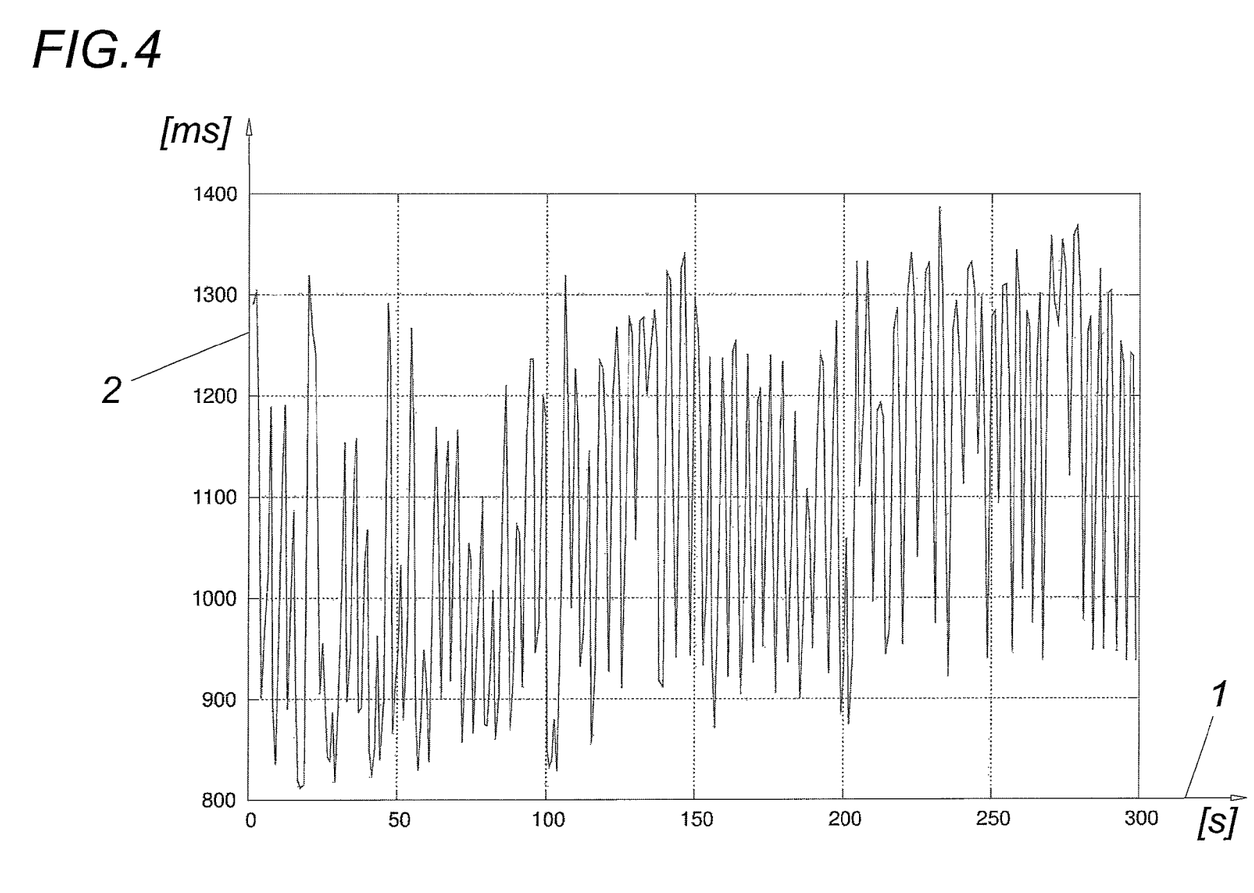

Furthermore, the informational content of the values according to FIG. 2 can also be reproduced, in known manner, as a scatter plot (scatterplot) in accordance with FIG. 3. Such a bivariate statistical analysis in the time domain can take place, for example, on the basis of two consecutive RR intervals. In this connection, the duration of each heart beat 10 is plotted on the x axis as a function of the duration of the heart beat that follows this heart beat, in ms, on the y axis 11. One speaks of an advantageous regulation width, in other words of a comparatively good heart rate variability, if the plotted points in this diagram yield an essentially ellipsoid cloud of points, whereby the main axis of this point cloud lies essentially above the diagonal 12 that has been drawn in. Points that lie on this diagonal refer to two consecutive RR intervals having the same length.

The possible evaluation of such representations according to FIGS. 1-3 with regard to the physical and/or psychological state of a subject, particularly also on the basis of the width of an ellipsis in the scatter plot, of a symmetrical, left-steep or right-steep Gauss curve, of density distributions in the histogram, etc. are known and discussed in detail in the prior art.

According to the invention, the analysis of the heart rate variability (HRV) now comprises at least one investigation of at least one frequency distribution for multimodal distribution.

Figure 5:
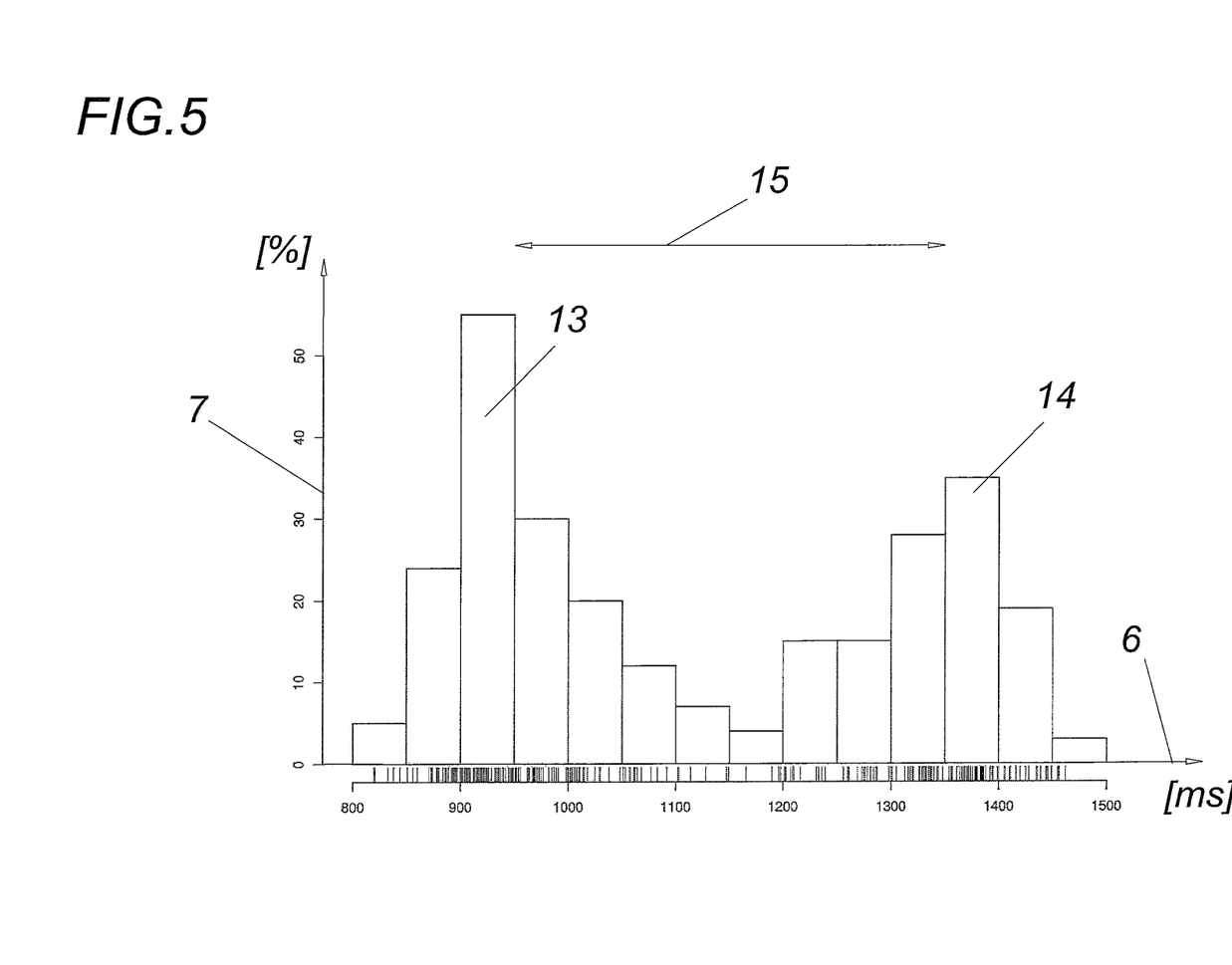
Figure 6:
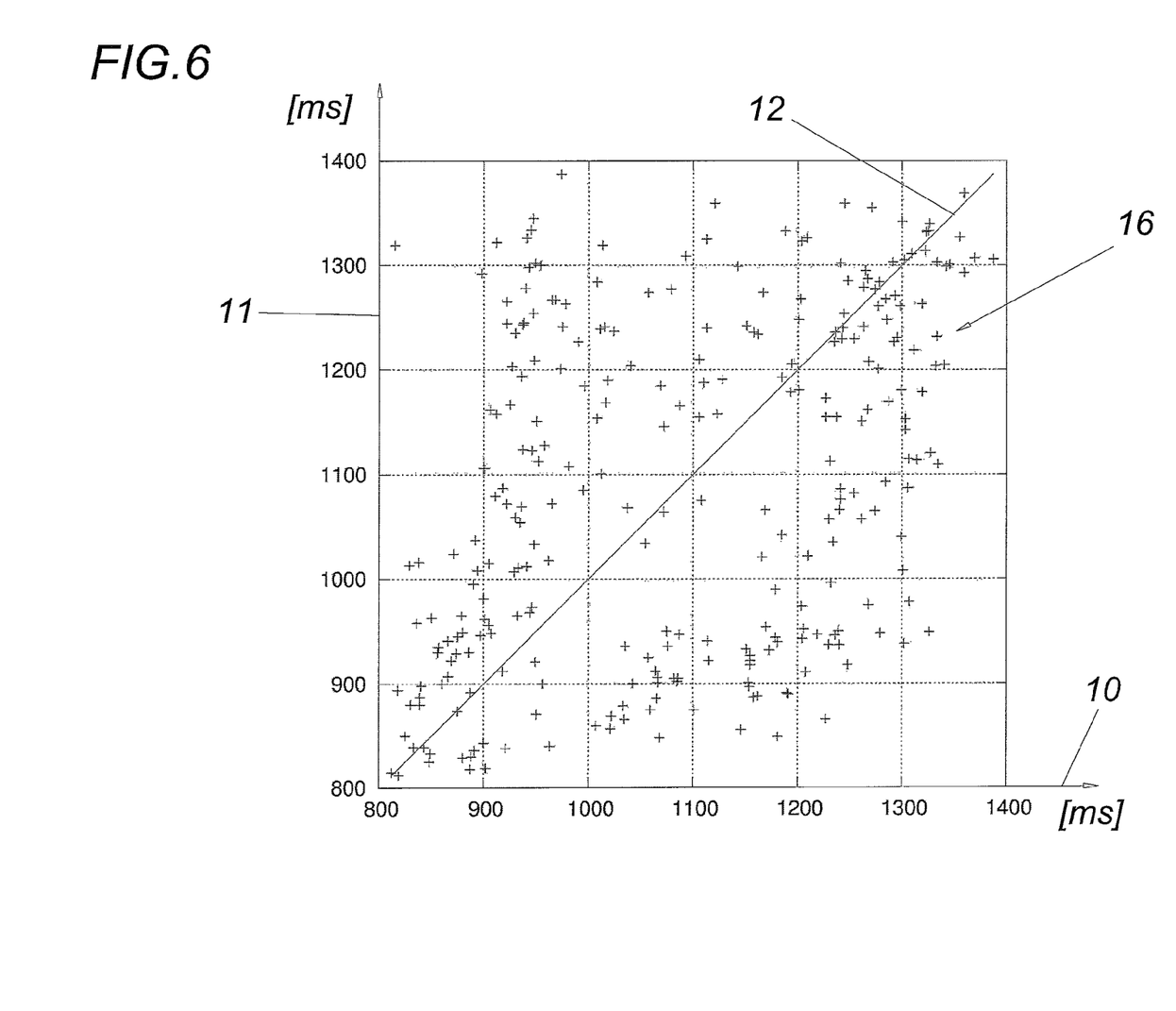

In order to illustrate this, an example for the result of a different RR interval measurement is shown in FIGS. 4 to 7—corresponding to the preceding figures. In FIG. 5, a multimodal distribution can be seen, specifically by means of the formation of two maxima 13, 14, which form a modus, in each instance. It should be pointed out that the histograms according to FIGS. 2 and 5 should also be understood as examples of representations, and of course assignments of the classes, scales, and units of the x or y axis can or must be undertaken in order to allow implementation of the method according to the invention. To assess the state of a subject, the spacing 15 of determined parameters of the modal distributions relative to one another—here, maxima—can be used as a measure, for example. In accordance with such recognitions, it should be possible to classify a psychological and/or physical state of a subject all the more advantageously, the greater the distance between two modes. In this connection, it might also be necessary to take the difference in the heights of two or more determined maxima or modes relative to one another into consideration, or other parameters of the modal distribution, such as a calculation of the density distribution, can also offer significant information in this regard. From the example of FIG. 5, with a frequency distribution of two maxima 13, 14, it can specifically be derived, among other things, that the average heart rate could form essentially by means of two basic oscillations, as has already been explained.

FIG. 6 once again shows a scatter plot 16, on the basis of which it becomes evident that an analysis of the frequency distribution can be comparatively difficult, because the values entered in the scatter plot appear in the manner of a shotgun shot. It can be seen that the lengths of two consecutive heart beats essentially differ—an ellipsoid frequency distribution as indications of it can be seen in FIG. 3, which is generally considered desirable, can be seen only with difficulty. It can furthermore be seen that comparatively many RR interval pairs are comparatively far away from the diagonal 12, which can permit the conclusion that the heart activity appears to be arrhythmic or non-harmonic, in other words deviating from a basic oscillation.

Figure 7:
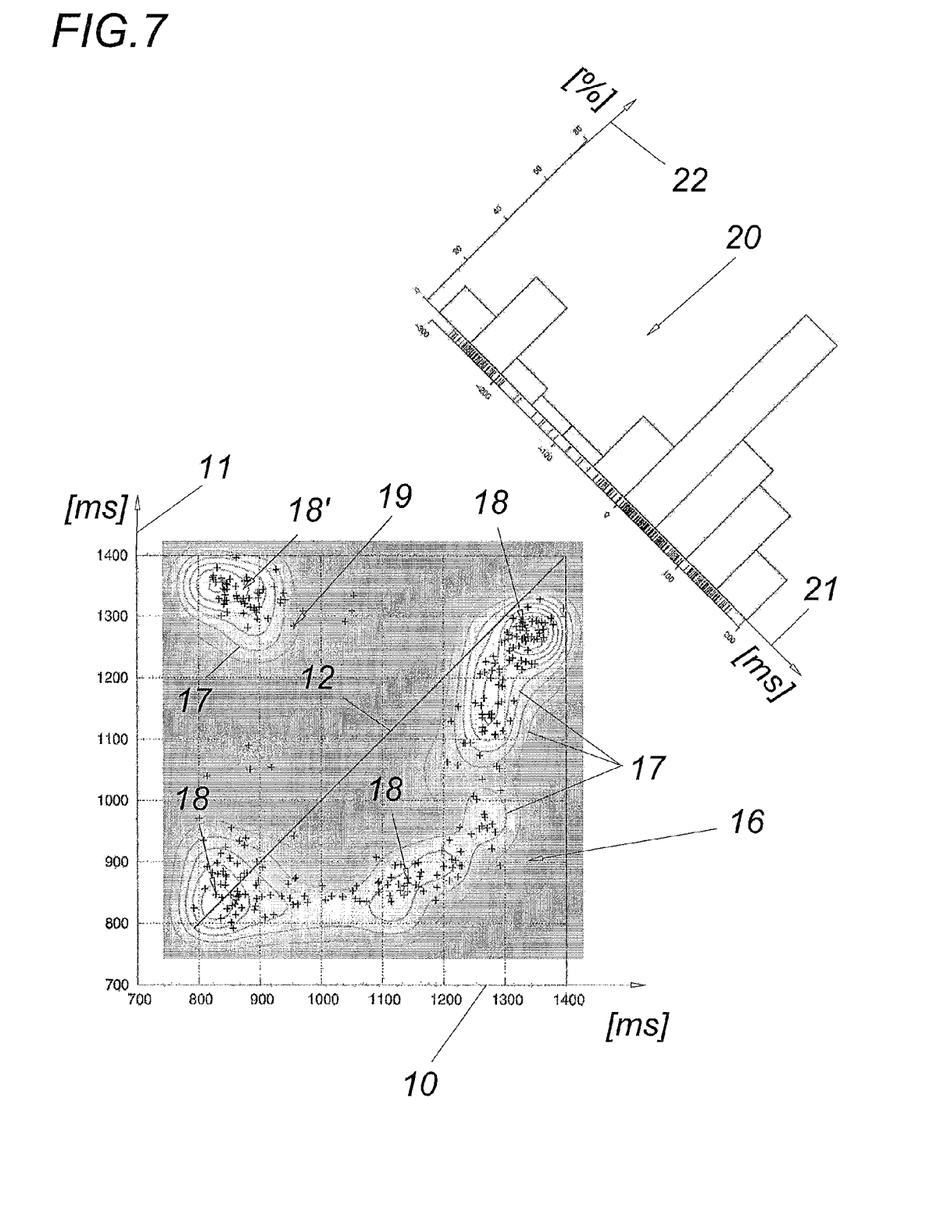

It is important, according to the invention, to investigate the scatter plot for a multimodal distribution. A possible exemplary embodiment is shown in FIG. 7, whereby, of course, any other type of representation of modal values can be suitable. In this example, modal values are represented as a density distribution, and their manifestations are characterized in the form of height lines 17. It is advantageous that in this way, rapid and meaningful information concerning modes 18 that are present, with regard to the duration of two consecutive RR intervals and/or the ratio of their RR interval duration relative to one another can be made possible. Also, possible values evaluated merely as outliers 19 can be used for analysis, in simple manner, or flow into it, in this way. It proved to be particularly advantageous that for this method according to the invention, a measurement duration of RR intervals over a time period of a few minutes can already be sufficient. It is therefore possible, among other things, to identify those modes 18 that result from frequencies of RR interval lengths as a function of the length of their subsequent RR interval and essentially determine the heart rhythm during the measurement interval. Accordingly, conclusions concerning the psychological and/or physical state of a subject are possible, for example on the basis of the location and/or—depending on the representation—the size, height or manifestation of individual modes in the scatter plot and/or, for example, also on the basis of the distance between the modes. 18', for example, shows a mode that can generally be viewed as being comparatively disadvantageous, because it characterizes consecutive RR interval lengths that differ comparatively greatly from one another or can characterize sudden changes in the heart rhythm. It should be stated that it is also possible to create three-dimensional scatter plots, in which each heart beat interval is plotted on the y and z axis as a function of its two subsequent heart beat intervals.

FIG. 7 furthermore shows a frequency distribution of the RR interval measurement as a histogram 20, which can be understood in the manner of a projection of the scatter plot 16. In this connection, the bivariate statistical analysis comprises classification of the frequency distribution as a function of the differences between two consecutive interbeat interval lengths. This histogram 20 can particularly allow investigation regarding multimodal distribution of RR intervals, which differ from their subsequent RR intervals with regard to their length.

Thus, those consecutive RR interval pairs having the same length, which therefore lie on the diagonal 12 of the related scatter plot, are assigned to the number 0 of the x axis 21 of the histogram in FIG. 7. This x axis 21 characterizes the extent of the difference between two consecutive RR interval lengths.

The y axis 22 of the histogram in turn indicates the frequency of the RR interval pairs. In the histogram 20 of FIG. 7, an investigation regarding multimodal distribution is also carried out; this can provide information, for example, as to the modes of which the heart rhythm is essentially composed over the examination time period, in each instance, or how suddenly subsequent RR intervals differ or change with regard to their length. Thus, it is possible, among other things, if a multimodal distribution occurs, to assume a deviation from a basic oscillation that essentially determines the average heart rate.

It is also possible to change and/or to facilitate the representation of the modal values. In FIG. 7, for example, it would be possible, in this connection, to blank out those RR intervals that correspond to the number 0 on the x axis 21, or—depending on the definition—come close to it, from the graphic representation. Thus, analysis of those modes that are formed by consecutive RR intervals that differ in length and are viewed as being more disadvantageous can be facilitated.

In this manner, furthermore the innervation of the vegetative nervous system during the measurement procedure—for example due to physical activity, sensory perceptions of the subject, etc.—can furthermore be taken into consideration. This can be advantageous because such innervation during the course of measurement of RR intervals can have the result of acceleration or slowing of the pulse, and thus of a change in the lengths of RR intervals. These variations, however, are viewed as being physiologically advantageous, as long as consecutive RR intervals are about of the same length—or, in accordance with a specific definition, approximately of the same length—and therefore have to be taken into consideration in the analysis of heart rate variability only with limitations. In this way, an additional possibility for interpretation or analysis of a manifestation and frequency of—sudden—changes of consecutive RR interval lengths can be obtained. Improved representation or analysis in the form of a histogram, scatter plot, etc., can thereby be made possible.

The invention claimed is:

1. Method for determination of the physical and/or psychological state of a subject based on an analysis of a heart rate variability (HRV) of the subject, the method comprising steps of:
   recording a first set of interbeat intervals of the subject during a first examination time period using a device with a sensor;
   generating a first frequency distribution of the first set of interbeat intervals in the time domain;
   investigating the first frequency distribution with regard to a first multimodal distribution to obtain information concerning heart activity; and
   determining the physical and/or psychological state of the subject based on the information concerning heart activity.

2. Method according to claim 1, wherein RR intervals of the heart and/or distances between pulse waves are used as interbeat intervals.

3. Method according to claim 1, wherein a classified frequency distribution is used.

4. Method according to claim 1, wherein the investigation of the first frequency distribution takes place on the basis of a univariate statistical analysis.

5. Method according to claim 1, wherein the investigation of the first frequency distribution takes place on the basis of a bivariate statistical analysis.

6. Method according to claim 5, wherein at least one interbeat interval with its subsequent interbeat interval is used for the bivariate statistical analysis.

7. Method according to claim 6, wherein a correction value, as a function of the difference of their lengths, is taken into consideration in the analysis for the consecutive interbeat intervals.

8. Method according to claim 5, wherein the bivariate statistical analysis comprises classification of the first frequency distribution as a function of the differences between two consecutive interbeat interval lengths.

9. Method according to claim 1, wherein the analysis of the heart rate variability takes into consideration the distance between modal values.

10. Method according to claim 1, wherein the analysis of the heart rate variability takes into consideration a ratio of densities of modal distributions.

11. Method according to claim 1, wherein in the determination of the physical and/or psychological state of the subject, the analysis data of the heart rate variability (HRV) are put into relation with comparison data of other subjects.

12. Method according to claim 1, wherein modal values of the first frequency distribution are determined using a threshold value.

13. Method according to claim 1, further comprising steps of:
   recording a second set of interbeat intervals of the subject during a second examination time period using the device with the sensor; and
   generating a second frequency distribution of the second set of interbeat intervals in the time domain;
   wherein different physical and/or psychological stress states act on the subject during the second examination time period as compared to the first examination time period.

14. Method according to claim 1, further comprising a step of:
   calculating a correction value for a time domain analysis of the heart rate variability, for parameters RMSSD and/or pNN50.

15. Method according to claim 1, wherein one parameter, in each instance, is determined from at least two modal distributions, the comparison result of which parameter is taken into consideration in the analysis of the heart rate variability (HRV).

16. Method according to claim 1, wherein the analysis of the heart rate variability takes into consideration a ratio of the integrals of densities of the modal distributions.

17. Method according to claim 1, wherein the same parameter, in each instance, is determined from at least two modal distributions, the comparison result of which parameter is taken into consideration in the analysis of the heart rate variability (HRV).

* * * * *